United States Patent [19]

Seidl et al.

[11] Patent Number: 4,976,263
[45] Date of Patent: Dec. 11, 1990

[54] EQUIPMENT FOR THE TREATMENT OF LYMPH BLOCKAGES AND THE LIKE

[75] Inventors: Hans Seidl; Wolfgang Walder, both of Amberg; Walter Reinhold, Schnaittach b. Nbg., all of Fed. Rep. of Germany

[73] Assignee: Physiomed-Medizintechnik GmbH, Fed. Rep. of Germany

[21] Appl. No.: 178,147

[22] Filed: Apr. 6, 1988

[30] Foreign Application Priority Data

May 20, 1987 [DE] Fed. Rep. of Germany ....... 3716816

[51] Int. Cl.⁵ .......................... A61N 1/40; A61N 1/04
[52] U.S. Cl. .................................. 128/421; 128/798; 128/800
[58] Field of Search ................. 128/421, 422, 423 R, 128/783, 798, 795, 796, 800, 801, 802, 381, 24.1, 24.5

[56] References Cited

U.S. PATENT DOCUMENTS

| | | | |
|---|---|---|---|
| 1,536,273 | 5/1925 | Schnee | 128/800 |
| 4,033,356 | 7/1977 | Hara | 128/801 X |
| 4,846,178 | 7/1989 | Fuxue et al. | 128/798 X |

FOREIGN PATENT DOCUMENTS

| | | | |
|---|---|---|---|
| 1181826 | 11/1964 | Fed. Rep. of Germany | 128/798 |
| 2191948 | 12/1987 | United Kingdom | 128/422 |

OTHER PUBLICATIONS

Geddes et al, "Stimulation with Capacitor Electrodes", Med. & Biol. Eng. & Comp., vol. 25, No. 3, May 1987, pp. 359–360.

*Primary Examiner*—Lee S. Cohen
*Attorney, Agent, or Firm*—Laff, Whitesel, Conte & Saret

[57] ABSTRACT

An equipment for the treatment of lymph blockages, hyperacidic musculature and the like, containing a switching circuit to generate a series of voltage impulses and two contact devices to apply these voltage impulses to a to-be-treated part of the body in order to achieve a mechanical vibration stimulation, is provided so that the switching circuit generates a series of high voltage impulses and contains a current limiting circuit, and that one of the contact devices has a high transfer resistance to human skin, while high filed intensities at higher mechanical loading capacity should be achieved.

9 Claims, 2 Drawing Sheets

EQUIPMENT FOR THE TREATMENT OF LYMPH BLOCKAGES AND THE LIKE

FIELD OF THE INVENTION

The invention is aimed at an equipment for the treatment of lymph blockages, hyperacidic musculature and the like containing a switching circuit to generate a series of voltage impulses and two contact devices to apply these voltage impulses to the part of the body being treated.

BACKGROUND OF THE INVENTION

Such equipments are known in various embodiments. They contain, as a rule, at least two electrodes, each of which has a possibly small transfer resistance to the skin surface of the patient to be treated, while the therapeutic effect is essentially based on the effect of the currents generated in the tissue through the applied electrodes. Direct current, direct current impulses, as well as alternating current, are used in the application. A special form of treatment is formed by the so-called interference current treatment, in which case through two pairs of electrodes crossing each other alternative currents with slightly different frequencies are applied, and then in the tissue a low frequency interference current is formed from the applied alternative currents of medium frequencies.

To apply such voltages and to generate the desired therapeutically effective currents, it is known to attach the electrodes, i.e. members with high conductivity, with the help of adhesive or clamping devices on the body. Further is known the attachment of electrodes on gloves, which are worn by the therapist, so that the respective place of the effectiveness of the electrode can be easily changed. At the same time care will be taken by forming the glove as a sponge glove and by dampening same or by similar measures, to keep the transfer resistance between the electrode and skin possibly low, to avoid uncomfortable sensations on the surface of the skin by comparatively high currents. The previously mentioned interference current treatment also has as its aim to confine currents, which are possibly strongly irritating for the skin, in the tissue structure.

SUMMARY OF THE INVENTION

Due to this, the invention sets the task to create an equipment for a differing from this, basically new form of treatment, where the effect of the currents inside the tissue matters less, and where the treated connective tissues or the muscles are stimulated to mechanical vibration, but which, in contrast to the stimulation by externally applied vibrator-massage equipment are modulated endogenously in the tissue inners.

The task will be solved according to the invention by the switching circuit generating a series of impulses of high voltage and containing a current limiting circuit, and one of the contact devices providing a contact surface with a high transfer resistance to the human skin. Preferably, the voltage of the applied impulses in between 100 and 600 V. Preferably direct current impulses will be used in this case.

By this development, in accordance with the invention, it will be achieved that in the human tissue itself only currents of extremely low amperage, i.e. of the order of micro-amperes, flow. This is caused by the high transfer resistance of at least one contact device, while the current limiting device assures, that when conditions differ from the normal, e.g. when the surrounding environment has a high humidity, there is no danger to the to-be-treated person from the relatively high voltage used. Because of the aim for low amperage, a battery or a storage battery may be used as the source of the voltage, while the direct current which is converted into a series of impulses can be correspondingly highly transformed. The force massaging the tissue is modulated periodically according to the stimulating frequency by the series of impulses applied to the to-be-treated part of the body, by which an extremely effective removal of blockages of lymph fluid, of hyperacidic musculature, haemorrhages and the like, can be achieved by an autonomous regeneration of the connecting tissue, i.e. the concentration accumulation in the tissue will be broken. The greater efficiency compared with the externally applied massage devices seems to be especially due to the endogenous modulation in this case. In contrast to the beforementioned known treatment equipments, the device of this invention causes no perception of current and can therefore be applied to extremely sensitive patients. The treated person perceives only a pulsation or vibration of the tissue the same as that of the body, equalling the pulse beat of the heart. Moreover, in this type of stimulation the application of such frequencies is possible, which can be produced only with difficulties by mechanical excitation. In contrast to the excitation with mechanical vibration devices, the exact control of the dynamics of the vibration movement is possible by using a corresponding impulse pattern.

According to the present state of knowledge the physiological-physical interrelations, which are individually responsible for the materialisation of this effect, not yet fully explained, although there are some indications that the effect can be traced back to a periodic change of the friction force between the glove of the therapist and the treated tissue due to a phenomenon similar to the Johnsen-Rahbeck effect. According to the Johnsen-Rahbeck effect, a force of attraction occurs when applying a voltage between a semiconductor plate and a metal plate, due to imcomplete point-like contact, which in turn influences the friction force in a relative movement. This effect is determined by the semiconductor-like behaviour of a plate, which in the present case is the material of the glove, which makes the formation of the charge concentration on the surface possible on one hand, but on the other hand avoids these accumulated charges being conducted away immediately due to a good conductivity, without achieving the necessary high potential difference.

The pulsating electrical field between the hand of the therapist and the body of the patient leads therefore to a pulsating electrostatic force of attraction, and with it to a pulsating friction force and this in turn, finally to a pulsating forming of the tissue, which can be also felt.

Furthermore, test have shown that, when using a very strongly insulating material for the glove, the observed effect is relatively weak and subsides quickly. However, with a glove of somewhat lower resistance a better effect is achieved. In addition, gloves with greater thickness can be used in practice, while in case of highly insulating materials an extremely thin material is necessary.

According to an advantageous embodiment the contact surface of the contact device is provided with a layer of synthetic material, particularly a layer of vinyl or the like. Such a synthetic material layer, without any additives for the increase of the conductivity, has the high transfer resistance, necessary for the application according to the invention, in comparison with the human skin and on the other hand satisfies the hygienic requirements demanded of a surface of this kind.

It could be conveniently arranged that one highly resistant contact device shaped as a glove, on whose internal side an electrode connected with the switching circuit is provided, and that the other contact device is formed as a conventional clamp electrode.

This arrangement enables, by maintaining the high transfer resistance of one electrode and preventing of a direct contact of same with the skin surface, i.e. by creating of a merely indicect contact through the external side of the glove, the realisation of the basic idea of the invention, while the basic advantages of a glove-electrode will remain. Advantageously in the case of this form of embodiment a vinyl glove or the like will be used as a glove, i.e. a glove, which contrary to the usual, sponge-like glove-electrodes, ensures a high transfer resistance.

Another embodiment according to the invention envisages that the high resistant contact device and the switching circuit are accomodated in the same housing. Due to the possibility of using a battery or a storage battery as the power source, the electrical supply line to the housing can be also dispensed with, so that the entire device can be built as a compact, easily manageable portable equipment. While doing this, the therapist can with his other hand touch the body of the patient, to establish the contact between the second contact situated in the handle of the equipment and the body of the patient.

The more pliable the tissue and the slower the movement of the therapist, the greater is the pulse width required to achieve the maximum force. The required pulse width is also correlated with the set of frequency, so that the setting of the touching conditions presents very good adjusting possibilities.

These will improved further because the impulse form is changeable. Through a suitable combination of touching conditions and impulse form, the induced in the tissue formation during compression in the direction of movement can be achieved at a different speed than during the following relaxation against the direction of movement. Because of the dependence of the internal friction force on the speed relationship, the direction of the force, acting on the tissue fluid, can be controlled by the therapist and thus the aimed fluid shifted.

In this sense it be further envisaged that the series of impulses will be amplitude or frequency modulated.

In place of the poor conducting material, well insulating foil can also be used. Then, due to the lack of self-discharge of the foil, a discharge circuit is provided for in the equipment. Moreover, due to the self-adjusting polarisation of the foil, voltage impulses with alternating directions should be used.

The beforementioned embodiments referred essentially to work with direct current impulse series. The strived for effect can also be achieved essentially with alternating current impulses. However, to achieve a marked effect when using alternating current impulses the contact surface must have very good insulating properties and switching circuit with quick-discharge circuit needs to be used, to avoid a build-up of static charge. Furthermore, when using, for example, a contact surface in the form of a glove, care should be taken that a very thin material is used.

To achieve an individually adjustable, optimum therapeutical effect each time, a device to change the touching conditions of the voltage impulses is provided. At the same time preferably a variable basic frequency, which can be approximately 30 Hz, is assumed.

The setting of the frequency and the touching conditions are advantageous. However, an impulse adjuster and a pause adjuster is provided here.

Further features, advantages and details of the invention can be seen from the following description of a preferred embodiment. based on a drawing.

DESCRIPTION OF A PREFERRED EMBODIMENT

Figure 1:
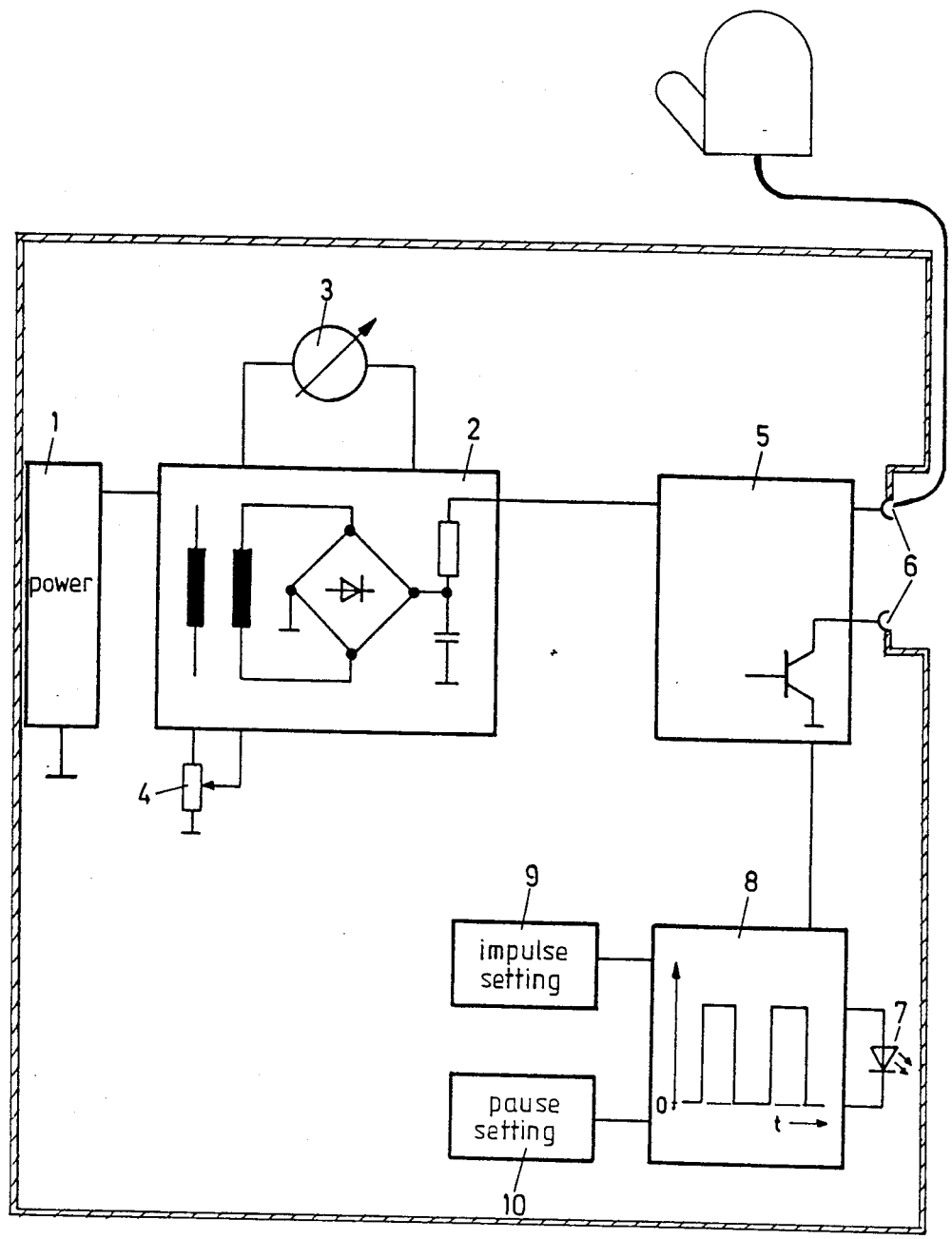
FIG. 1 is shematic block wiring diagram of a first embodiment of an equipment according to the invention.

According to FIG. 1 a power source 1 in the form of a battery is connected with a direct current transformer to increase the battery voltage, which has a current limiting device 2. An indicator 3 shows the actual output voltage.

In the direct transformer 2 an output stage 5 with electrode connecting sockets 6 is connected.

A signal generator 8 is connected to the output stage 5, to which an impulse setting device 9 and a pause setting device 10 for the setting of the touching conditions and the length of the impulse is assigned. An impulse indicator in the form of a light emitting diode 7 illustrates optically the emitted impulses.

Figure 2:
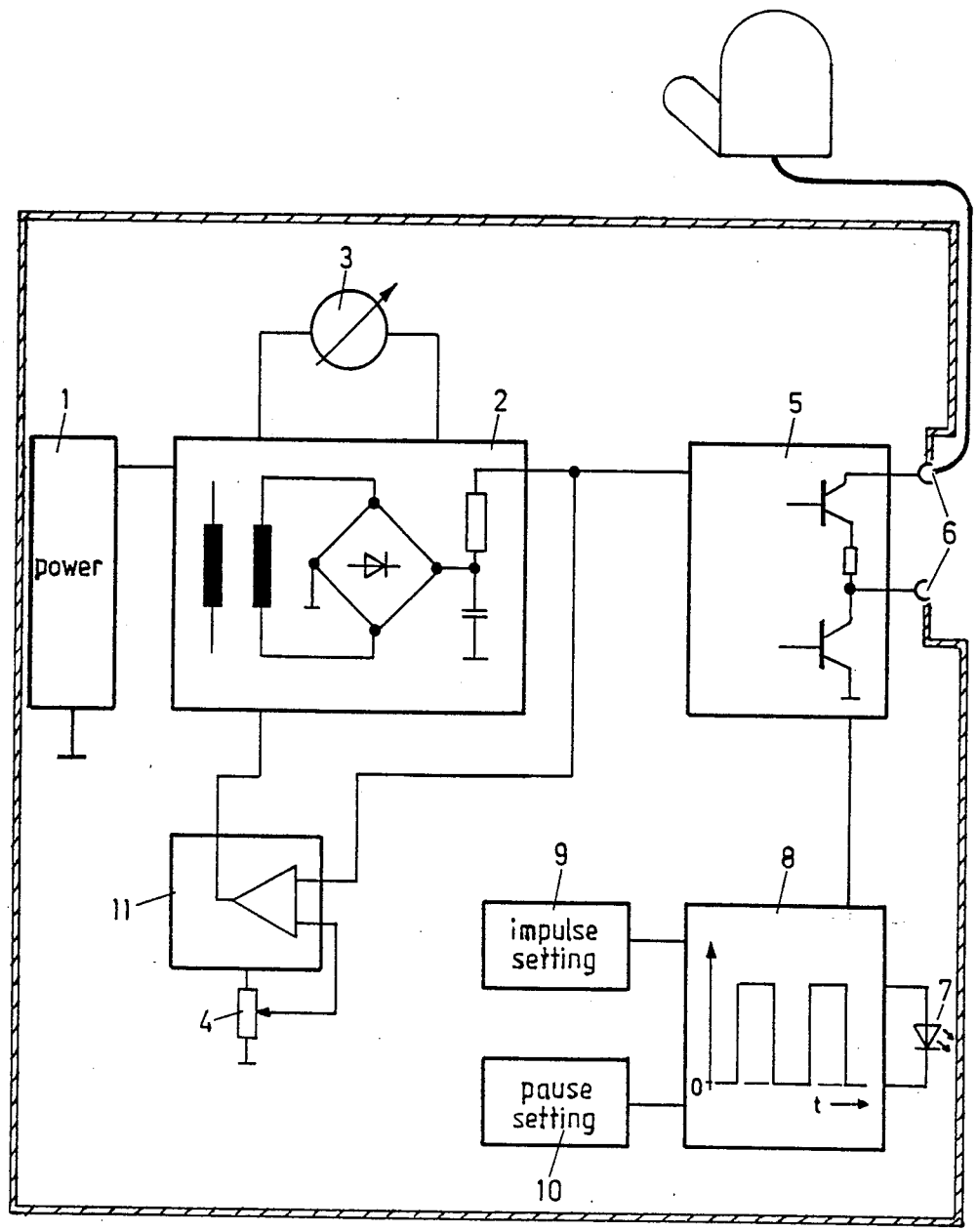
FIG. 2 is schematic block wiring diagram of a second embodiment of an equipment according to the invention.

In case of the illustrated in FIG. 2 embodiment the output stage 5 contains a fast discharge circuit built basically as a transistorswitch, which on the one hand provides the current limitation and on the other assures an active discharging of the patient, which is especially necessary when using a foil with very high resistance, as no self-discharge takes place then.

In case of a foil with low resistance such an active discharge is not necessarily required, but it improves the time reaction, i.e. the use of higher frequencies id feasible. Additionally or alternative the use of impulses of changing polarity counteracts the polarisation of foils with high resistance.

Additionally, the construction according to FIG. 2 has an arrangement 11 for keeping the voltage of the output circuit constant, which is assigned to a corresponding to FIG. 1 setting potentiometer 4 for the output voltage.

What is claimed is:

1. Equipment for the treatment of lymph blockages, hyperacidic musculature and the like comprising
   switching circuit means for generating a series of high voltage impulses with a variable frequency, the basic frequency being about 30 Hz;
   two contact means for applying said voltage impulse to a part of the body being treated; wherein one of the contact means has a contact surface formed by a vinyl layer with very good insulating properties;
   said switching circuit means further comprising a quick discharge and current limiting circuit formed by a switching transistor;

and wherein said first of said two contact means is shaped as a glove;

the internal side of said glove being provided with an electrode, said electrode being connected with said switching circuit means.

2. Equipment according to claim 1, wherein the switching circuit means generates voltages between 100 and 600 V.

3. Equipment according to claim 1, wherein the vinyl layer of said contact surface has a high transfer resistance to the human skin.

4. Equipment according to claim 1, wherein at least one of said contact means and said switching circuit means are accommodated in housing.

5. Equipment according to claim 4, wherein housing is provided with a handle.

6. Equipment according to claim 1, wherein said switching circuit means comprises means to change the duty ratio of direct current impulses.

7. Equipment according to claim 1, wherein means are provided to vary the impulse frequency.

8. Equipment according to claim 1, wherein means are provided to vary the form of the impulse.

9. Equipment according to claim 1, wherein means are provided to modulate the series of impulses in amplitude and/or in frequency.

* * * * *